United States Patent [19]

Kennedy et al.

[11] Patent Number: 5,062,169
[45] Date of Patent: Nov. 5, 1991

[54] CLINICAL BED

[75] Inventors: Earl W. Kennedy, Joplin; Robert D. Oexman; Larry Higgins, both of Carthage, all of Mo.

[73] Assignee: Leggett & Platt, Incorporated, Carthage, Mo.

[21] Appl. No.: 491,327

[22] Filed: Mar. 9, 1990

[51] Int. Cl.$^5$ ............................................. A47C 27/08
[52] U.S. Cl. ................................................. 5/449
[58] Field of Search .................... 5/453, 455, 449; 128/718, 721, 722, 723

[56] References Cited

U.S. PATENT DOCUMENTS

| | | | |
|---|---|---|---|
| 3,727,606 | 4/1973 | Sielaff | 128/722 |
| 4,146,885 | 3/1979 | Lawson, Jr. | 128/721 |
| 4,297,755 | 11/1981 | Mollura | 5/455 |
| 4,320,766 | 3/1982 | Alihanka et al. | 128/671 |
| 4,324,259 | 4/1982 | Wright | 128/722 |
| 4,438,771 | 3/1984 | Friesen et al. | 128/671 |
| 4,444,199 | 4/1984 | Shafer | 128/691 |
| 4,509,527 | 4/1985 | Fraden | 128/671 |
| 4,602,644 | 7/1986 | DiBenedetto et al. | 128/721 X |
| 4,662,012 | 5/1987 | Torbet | 5/453 |
| 4,681,098 | 7/1987 | Lee | 128/630 |
| 4,827,763 | 5/1989 | Bourland et al. | 128/722 X |
| 4,834,109 | 5/1989 | Watson | 128/721 |
| 4,838,275 | 6/1989 | Lee | 128/670 |
| 4,860,766 | 8/1989 | Sackner | 128/721 X |
| 4,862,144 | 8/1989 | Tao | 128/721 X |
| 4,864,671 | 9/1989 | Evans | 5/455 X |
| 4,895,160 | 1/1990 | Reents | 128/722 X |
| 4,935,968 | 6/1990 | Hunt et al. | 5/453 |

FOREIGN PATENT DOCUMENTS 09650 12/1988 World Int. Prop. O. ............ 5/455

Primary Examiner—Gary L. Smith
Assistant Examiner—Michael J. Milano
Attorney, Agent, or Firm—Wood, Herron & Evans

[57] ABSTRACT

A clinical bed system for monitoring and recording movements of a person while reclining or sleeping on a bed of the system. The bed includes an air mattress having multiple isolated air-filled zones. Attached to each of these zones is a pressure-responsive readout device which is operative to read out and record pressure changes resulting from movement of a person reclining on the air mattress.

11 Claims, 2 Drawing Sheets

CLINICAL BED

This invention relates to bedding systems for monitoring movement of a person lying on a bed and, more particularly, to a bedding system for monitoring abnormal movements of a sleeping person for purposes of diagnosing sleep disorders.

BACKGROUND OF THE INVENTION

Sleep disorders are very common with millions of adults in the United States alone reported as having trouble with sleeping to such an extent that they require consultation with a physician. Two very common types of disorders are sleep apnea and periodic leg movement.

Periodic leg movement is characterized by unilateral or bilateral leg twitches that repeat every 20 to 40 seconds. Episodes may last from 5 minutes to 2 hours and alternate with periods of normal sleep. Such movements cause fragmented or unrefreshing sleep.

Sleep apnea is characterized by a cessation of breathing. Such cessation varies with different types of sleep apnea from a cessation of airflow with a lack of respiratory effort to a cessation of airflow in the presence of continued thoractic movements and exaggerated inspiratory efforts. Serious cases of sleep apnea may show over 500 apneas per night, each one lasting 10 to 120 seconds, none of which is usually remembered by the sleeping person who may be aroused by the apnea.

Medical diagnoses of these two common sleep disorders now follows a standard protocol. About one hour before bedtime, the sleeper arrives at the laboratory, fills out some questionnaires, and has electrodes and sensors applied to his body. Electrodes are applied to the scalp, eye, chin, and earlobes. These sensors remain on the body for the course of a night's sleep in order to measure airflow, respiratory effort, EKG, and surface EMG over the right and left tibias. This is a very expensive procedure and because of the expense, makes follow-up treatment difficult.

PRIOR ART

There have been attempts to measure movements of a person in a bed and, particularly, a sleeping person, without the attachment of sensors, electrodes, and other devices which may interfere with obtaining a true pattern of a person's sleeping movements. Such a system is depicted in U.S. Pat. No. 4,320,766 which utilizes a capacitive motion sensor beneath a mattress for monitoring movements of a person atop the mattress.

Other patents which disclose systems for detecting cessation of movement of a body on a sleeping surface are disclosed in U.S. Pat. Nos. 4,438,771; 4,444,199; 4,509,527; 4,681,098; and 4,838,275. But, the systems disclosed in all of these patents are not used for monitoring movements in a bed for purposes of diagnosing sleep disorders, primarily because of the lack of sensitivity of the systems and/or the expense of the systems.

SUMMARY OF THE INVENTION

It has been an objective of this invention to provide a bedding system which is capable of monitoring movements of a person sleeping atop a mattress of the system.

Still another objective of this invention has been to provide an economical, non-invasive bedding system which is capable of monitoring even small movements of a person sleeping atop a mattress.

These objectives are achieved and this invention is predicated upon the concept of monitoring the movements of a person while sleeping on an air mattress which has multiple, air-filled, isolated zones. At least one of those zones, and preferably four of these zones, are connected to a pressure-responsive readout device which is capable of measuring pressure changes per unit of time in that one zone. These pressure changes are indicative of movements of the person residing atop that zone so that a medical doctor utilizing the readouts can diagnose sleep disorders from the readout.

The apparatus employed in the practice of this invention comprises a fluid-filled air mattress having multiple, isolated zones, each zone of which is maintained at a prescribed pressure. Attached to at least one, but preferably four, of the zones of the mattress is a pressure-responsive readout device in the form of a stylus recorder connected through a pressure transducer to the zones. The stylus recorder provides a visual readout of pressure changes in the zones to which the recorder is attached, which pressure changes are, in turn, reflective of movements which occur on the bed over that zone.

While the invention of this application is described specifically in terms of a system for monitoring movements of a person reclining on a bed for purposes of diagnosing sleep disorders, this system is equally useful for monitoring movements of a person reclining atop the bed for other purposes, as for example, monitoring breathing, abnormal movements, such as are characteristic of epileptic seizures, and any other type of movement which requires remote monitoring of a person while sleeping.

The primary advantage of this invention is that it provides a comfortable, economical, practical, non-invasive system for monitoring movements of a person while reclining or sleeping on a bed. Furthermore, it provides such a movement monitor in a system which is conducive to sleep rather than an interference with sleep. Additionally, because of the simplicity of the equipment utilized in the practice of the invention, it may be easily transported, and for that reason, may be set up in a person's home so as to facilitate prescreening and medical follow-up and treatment of a patient's medical condition at a minimal expense to the patient and the treating physician.

DESCRIPTION OF THE DRAWINGS

These and other objects and advantages of this invention will be more readily apparent from the following description of the drawings in which.

DETAILED DESCRIPTION OF THE INVENTION

Figure 1:
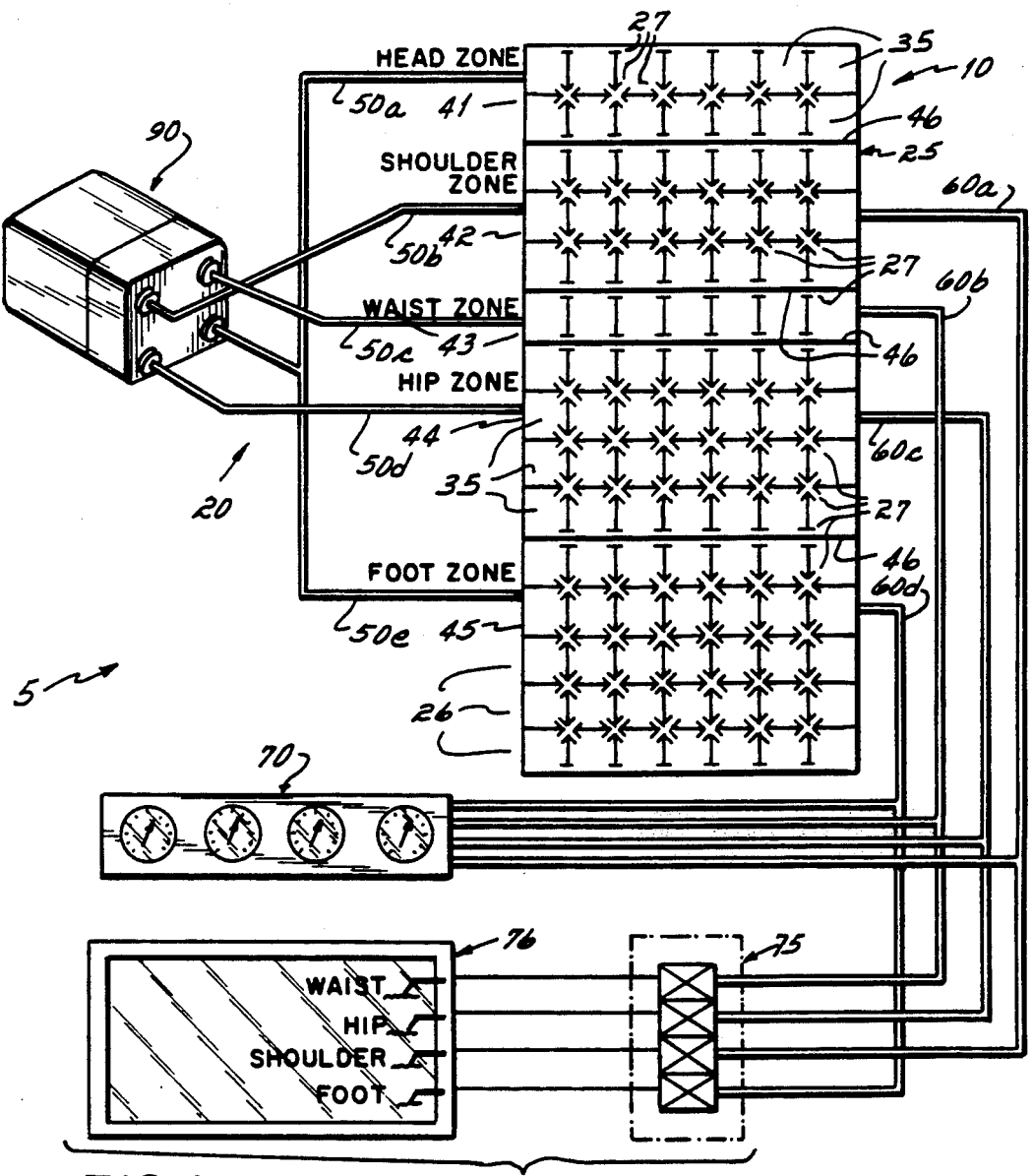
FIG. 1 is a schematic illustration of a clinical bed system incorporating the invention of this application.

With reference first to FIG. 1, there is diagrammatically illustrated a clinical bed apparatus or system 5. This clinical bed system comprises an air bed 10 and a readout device 15. The air bed 10 comprises an air mattress 25 and an airflow control system 20 for supplying air pressure to and exhausting air pressure from the air mattress 25. The air bed 10, including the airflow control system 20, is completely disclosed in U.S. patent application Ser. No. 07/256,902, filed Oct. 12, 1988, and assigned to the assignee of this application. For purposes of more completely describing this air bed, the disclosure of that application is hereby incorporated by reference.

AIR MATTRESS

Figure 2:
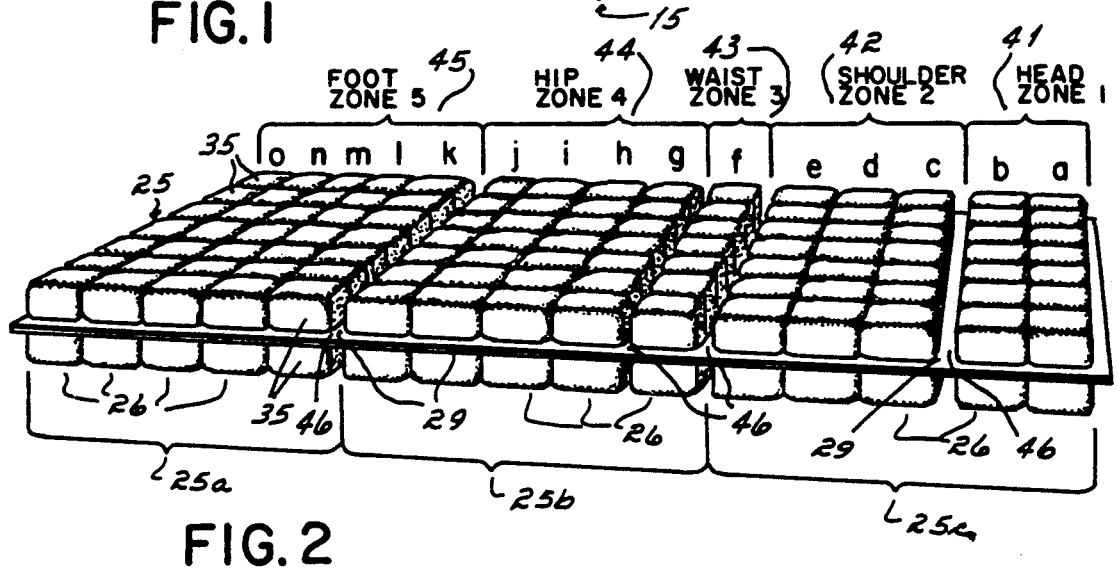
FIG. 2 is a perspective view of the air mattress of FIG. 1.

The mattress 25 is formed from three separate, individual sections 25a, 25b, 25c which, when placed end-to-end, as illustrated in FIG. 2, form a complete mattress. As illustrated in FIG. 2, each section comprises five transverse rows 26 of cells 35, each row 26 of which in the illustrated embodiment is seven cells wide.

Each mattress section 25a, 25b, 25c is formed from two sheets of 40 mil (0.040 inches) vinyl. Each sheet is heated and vacuum formed to provide a series of recesses or pockets. The two sheets overlie each other with the pockets facing each other. The sheets are sealed around the edges 29 and between adjoining pockets, except at the intersecting corners of the pockets of each zone of the mattress as explained more fully hereinafter.

The pockets are square in cross section with the seals 29 being formed between adjacent pockets in order to form the cells 35. Within any one zone, adjacent cells are interconnected by channels 27 of between ¼ inch to ½ inch in width. These channels, located at the corners between adjacent cells of each zone, are not illustrated in the drawings except diagrammatically at 27 in FIG. 1. The gap or width of the channels 27 between adjacent cells within any zone is sufficient to permit a uniform distribution of air among all the cells of a zone and permit the shifting of air from cell to cell as a sleeper shifts his position on the mattress.

Each pocket is approximately 4 inches deep so that each cell 35 is about 8 inches in overall height. Each cell is about 5 inches across opposed sides. The square cells, when inflated, have rounded, but substantially flat, ends.

The mattress 25 is divided into five zones. Zone 1, formed by two rows a and b and indicated at 41, is a head zone which extends from the upper end of the bed to about the neck area of a person reclining atop the bed. Zone 2, formed by rows c-e and indicated at 42, is a shoulder zone which underlies the shoulder area from the waist to the neck of a person reclining atop the bed. Zone 3, formed by a single row f and indicated at 43, is a waist zone which underlies the waist of a person reclining atop the mattress. Zone 4, formed by rows g, h, i, and j and indicated at 44, is a hip zone which receives the hips and pelvic area of a person reclining atop the mattress. The fifth and last zone, Zone 5, formed by rows k-o and indicated at 45, is a foot zone which receives the legs and feet of a person reclining atop the mattress. Four continuous transverse seals 46 close the gaps between adjoining cells and divide the mattress into five zones 41-45.

Each zone 41-45 has an air connection hose, indicated at 50a-50e, respectively, which connects the zone to the airflow control system 20. That system 20 includes an air pump and pressure regulators contained within a housing 90. That system 20 is operative to supply air to each of the zones to maintain those zones at predetermined pressure levels. When the pressure in a zone is too high, a diaphragm-type pressure regulator (not shown) within the housing 90 is operative through the associated connecting hose 50 to permit air to bleed out of the zone to atmosphere. And, when pressure is too low, the diaphragm-type pressure regulator associated with the zone opens to connect the air pump to the zone so as to introduce more air into the zone. The airflow control system 20 in practice is operative to maintain the preset pressures of the zones within plus or minus 5 percent of the preset pressure.

Each zone, the respective rows and cells comprising it and the preferred air pressure in it, are set forth in the chart below:

| Zone | Body Section | Rows | Water Pressure | Pressure Hg |
|---|---|---|---|---|
| 1 | head | a,b | 4" H$_2$O | 7.5 mm Hg |
| 2 | shoulder | c-e | 6" H$_2$O | 11.2 mm Hg |
| 3 | waist | f | 11" H$_2$O | 20.5 mm Hg |
| 4 | hip | g-j | 8" H$_2$O | 14.9 mm Hg |
| 5 | foot | k-o | 4" H$_2$O | 7.5 mm HG |

By combining Zones 1 and 5, the head and foot zones, a minimum of four different pressures can be employed in the five zones. To that end, the head and foot zones are connected to a common pressure regulator as is fully described in the above-identified application which has been incorporated by reference herein. Alternatively, zones 1 and 2, the head and shoulder zones, may be interconnected.

When a person reclines on the top of the mattress 25, the body weight of that person causes the air pressure in the zones to increase. The respective pressure regulators then operate to bleed air from the respective zones to atmosphere until such time as the zone pressures reach the pressure settings of the regulators. When the person leaves the mattress, the air pressures in the respective zones fall. The pressure regulators are then operative to permit flow into the zones until such time as the zone pressures are once again reestablished.

PRESSURE CHANGE READOUT DEVICE

In order to read out movements of a person reclining atop the mattress 25, the readout device 15 is provided. This readout device is in effect a pressure monitor operative to readout and record pressure changes per unit of time within each of the shoulder, waist, hip, and foot zones, respectively, of the mattress. In order to effect that readout, a hose 60a-60d is connected to each of the shoulder, waist, hip, and foot zones, respectively. These hoses are each connected to a dial-type pressure readout device 70 and to a four-channel pressure preamp 75 which converts pneumatic pressure signals to electronic signals, which electronic signals vary in amplitude with pressure changes. The electrical signals from the four-channel pressure preamp 75 are then fed into a stylus recorder 76, the output of which reflects the amplitude of movements on the bed over a period of time.

One four-channel pressure preamp which has been found suitable for use in this application is manufactured by E. J. McGowan and Associates of Elmhurst, Ill. It comprises four pressure transducers operative to convert pressure changes to electrical signals. A stylus recorder which has been found to be suitable for use in this application is a Kipp and Zonen Company Modular Vertical Face Stylus Recorder manufactured by Kipp and Zonen Company of Delft, Holland, with sales offices in Bohemia, N.Y., U.S.A. It comprises a four-module frame with pen offset compensation and a preamplifier module with 14 span from 1 microvolt to 10 volts full scale. Of course, any other conventional type of visual readout device which will read and convert the pressure output signals to visible time records would be suitable for use in connection with this invention.

OPERATION

In the use of the invention of this application to monitor movements of a person in a bed, the device is generally turned on before the subject enters the bed. The subject person then moves onto the bed in a reclining position with their waist located over the waist zone of the mattress. Thereby, the person is properly positioned on the bed.

Figure 3:
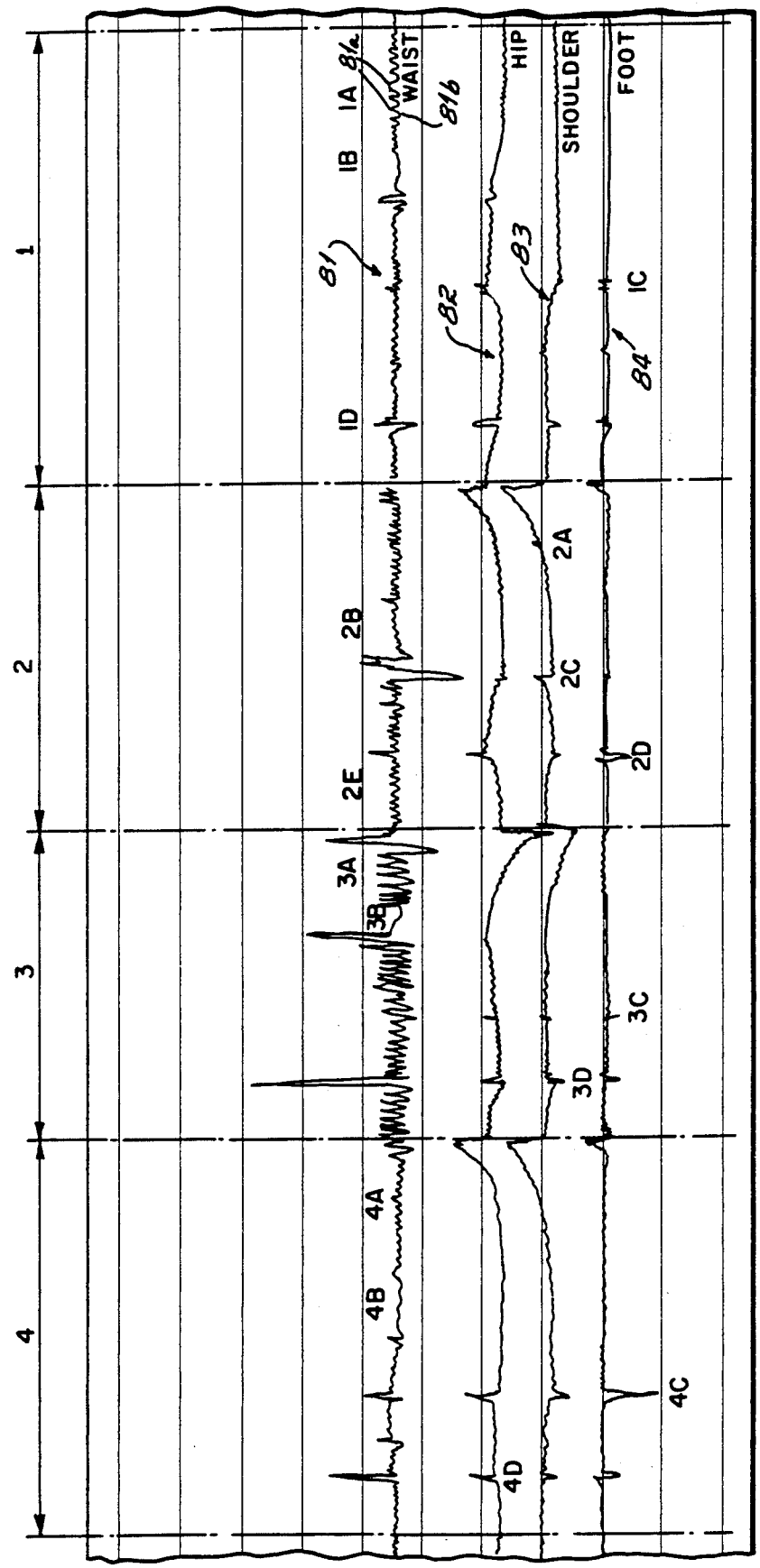
FIG. 3 is a readout record of movements of a person sleeping atop the mattress of the system illustrated in FIG. 1.

With reference to FIG. 3, there is illustrated a chart produced by the Kipp and Zonen recorder described hereinabove. The uppermost wave band 81 of this chart is connected to the waist zone 43 of the mattress, the second wave band 82 is connected to the hip zone 44, the third wave band 83 is connected to the shoulder zone 42, and the lowermost band 84 is connected to the foot zone 45 of the mattress. This printout of these four different wave forms represent pressure changes in each of the zones which are generated by a person sleeping atop the mattress 25. As will be readily apparent from this chart, the uppermost wave band, that which is connected to the waist zone 43 of the mattress, is the most sensitive because it is the zone of smallest volume. This zone is sufficiently sensitive as to enable breathing of a person reclining atop the mattress to be visually readable in the form of spikes 81a and valleys 81b on the chart. The other zones also reflect the same breathing pattern, but to a much less degree.

In the use of the clinical bed of this invention to diagnose sleep disorders, one protocol which might be used if the doctor desires a readout of the patient's position on the bed, as well as movements, is to place the patient atop the mattress and turn on the readout device 15 so as to record or "fingerprint" movements of that particular patient on the bed. As a result of this fingerprinting, the doctor making the diagnoses will thereafter be able to use that portion of the chart to interpret and read the results achieved when the recorder is utilized while the patient sleeps atop the mattress.

Still with reference to FIG. 3, that portion of the chart of FIG. 3 designated by the numeral "1" represents a pattern which was generated by a patient over a period of six minutes while sleeping on their back. The portion designated by the numeral "2" represents the same patient after that patient had moved to their side, in which position the patient remained for slightly over four minutes. The section designated by the numeral "3" represents a pattern generated after the patient had moved onto their stomach, in which position that patient remained for approximately four minutes. The Zone 4 is a pattern which was generated when the patient moved back onto their side.

Location 1A of this chart represents a normal breathing pattern while the person was resting on their back. At location 1B, the patient quit breathing for approximately 40 seconds, at location 1C, the patient had a leg jerk, and at location 1D, the patient had an arm movement.

Again, and still with reference to FIG. 3, it will be seen that at location 2A on the chart, the patient moved their arm. At location 2B, the patient quit breathing; at location 2C, there was an arm movement; at location 2D, a leg jerk; and at location 2E, there was a normal breathing pattern without any movement other than breathing movement.

When the patient moved to their stomach in Zone 3, the patient continued their normal breathing at location 3A on the chart; at location 3B, the patient again quit breathing; at location 3C, there was a leg jerk; and at location 3D there was an arm movement.

In Zone 4, there was a normal breathing pattern through the portion of the zone designated as 4A; at location 4B the patient stopped breathing for approximately 40 seconds; at location 4C there was a leg jerk; and at location 4D there was an arm movement.

It should now be readily apparent that the clinical bedding system 5 described hereinabove is very suitable for monitoring movement of a person reclining atop the mattress 25 of the system and that the system is sufficiently sensitive as to be suitable for use in diagnosing sleep disorders. It also, because of its relative simplicity and portability, is suitable for home use so that a medical doctor can place the system in a patient's home for prescreening, as well as for follow-up treatment, of a diagnosed sleep disorder.

While we have described only a single preferred embodiment of our invention, persons skilled in this art will appreciate changes and modifications which can be made without departing from the spirit of our invention. Therefore, we do not intend to be limited except by the scope of the following appended claims.

We claim:

1. Clinical bed apparatus for use in diagnosing sleep disorders by non-invasively monitoring a person reclining on a bed, which apparatus includes
   a bed for supporting a person reclining atop the bed, said bed having at least one isolated fluid-filled zone maintained at a pressure substantially above atmospheric pressure,
   readout and recording means including a readout and recording device, and connecting means extending between said readout and recording device and said fluid-filled zone, said readout and recording means being operative to measure and record movement of a person reclining on said bed as a result of fluid pressure changes in said fluid-filled zone measured and recorded on a record by said readout and recording device, said record being of a form and sufficiently sensitive to enable sleep disorders to be diagnosed from said record.

2. The apparatus of claim 1 which further includes a fluid pump and fluid control system for maintaining said fluid-filled zone at a preset pressure substantially above atmospheric pressure.

3. The apparatus of claim 1 wherein said one zone is filled with a gas.

4. The apparatus of claim 1 wherein said one zone is filled with air and wherein said readout and recording device includes a pressure transducer for converting pneumatic pressure signals to electrical signals and for feeding said electrical signals to an electrical signal-actuated stylus recorder.

5. The apparatus of claim 1 wherein said at least one zone comprises a plurality of interconnected cells, each cell of which is filled with fluid and is connected to adjacent cells of the zone by restricted fluid flow passages.

6. The apparatus of claim 1 wherein said bed includes an air mattress having at least three isolated air-filled zones for supporting a person reclining atop the bed, and means including a pneumatic pump and pneumatic control system for maintaining said zones at differing preset pneumatic pressures.

7. The clinical bed apparatus of claim 6 wherein said connecting means extends between said readout and recording device and each of said at least three zones and wherein said readout and recording device measures and records movements in each of said three zones.

8. A clinical apparatus for use in diagnosing sleep disorders by non-invasively monitoring a person reclining on a bed, which apparatus includes an enclosure having at least one fluid-filled zone maintained at a pressure above atmospheric pressure, readout and recording means including a pressure-responsive readout and recording device, and connecting means extending between said readout and recording device and said fluid-filled zone, said readout and recording means being operative to measure and recording movement of a person as a result of fluid pressure changes in said fluid-filled zone measured and recorded on a record by said readout and recording device, said record being of a form and sufficiently sensitive to enable sleep disorders to be diagnosed from said record.

9. The method of diagnosing sleep disorders by non-invasively monitoring a person while sleeping on a bed, which method comprises at least partially supporting a person on a fluid-filled enclosure while in a reclining position on a bed, which enclosure is maintained at a pressure substantially above atmospheric pressure, connecting the fluid-filled enclosure to a pressure-responsive readout and recording device, and while the person is sleeping with at least a portion of the body supported on the enclosure, measuring and recording the magnitude and duration of pressure changes in said enclosure with sufficient accuracy and sensitivity to enable sleep disorders to be diagnosed from the recording.

10. The method of diagnosing sleep disorders by non-invasively monitoring a person while sleeping on a bed, which bed includes a mattress having at least one fluid-filled zone, which zone is maintained at a pressure substantially above atmospheric pressure, which method comprises supporting the sleeping person while in a reclining position on the mattress with a portion of the person's body supported on said fluid-filled zone, connecting the fluid-filled zone of the mattress to a pressure-responsive readout and recording device, and while the person is sleeping on the mattress with at least a portion of the body supported upon the fluid-filled zone, measuring and recording the magnitude of the pressure changes of said fluid-filled zone with sufficient accuracy and sensitivity to enable sleep disorders to be diagnosed from the recording.

11. The method of diagnosing sleep disorders by non-invasively monitoring a person while sleeping on a bed, which bed includes a mattress having at least three fluid-filled zones, which zones are maintained at a pressure substantially above atmospheric pressure, which method comprises supporting the sleeping person while in a reclining position on the mattress with a portion of the person's body supported on each of said fluid-filled zones, connecting each of the fluid-filled zones of the mattress to a pressure-responsive readout and recording device, and while the person is sleeping on the mattress with at least portions of the body supported upon the fluid-filled zones, measuring and recording the magnitude of the pressure changes of each of said fluid-filled zones with sufficient accuracy and sensitivity to enable sleep disorders to be diagnosed form the recording.

* * * * *